United States Patent [19]

White

[11] Patent Number: 5,041,452

[45] Date of Patent: Aug. 20, 1991

[54] NOVEL DIAMIDES AND METHOD FOR IMPROVING FEED UTILIZATION AND LACTATION IN RUMINANT ANIMALS

[75] Inventor: Alan W. White, Kingsport, Tenn.

[73] Assignee: Eastman Kodak Company, Rochester, N.Y.

[21] Appl. No.: 414,157

[22] Filed: Sep. 28, 1989

Related U.S. Application Data

[60] Division of Ser. No. 297,898, Jan. 17, 1989, Pat. No. 4,895,951, which is a continuation-in-part of Ser. No. 81,048, Aug. 3, 1987, abandoned.

[51] Int. Cl.$^5$ ............................................. A01N 43/42
[52] U.S. Cl. .................................... 514/313; 424/442; 424/465; 546/108; 546/141; 546/142; 546/146; 546/147; 546/153; 546/156; 546/158; 546/170; 546/175; 546/291; 546/336; 514/352
[58] Field of Search .............. 546/336, 108, 141, 142, 546/146, 147, 153, 156, 158, 170, 175, 291; 424/442, 465; 514/313, 352

[56] References Cited

U.S. PATENT DOCUMENTS

| | | | |
|---|---|---|---|
| 2,890,980 | 6/1959 | Hotchkiss et al. | 424/442 |
| 3,531,563 | 9/1970 | Klothen et al. | 424/442 |
| 3,696,189 | 10/1972 | Snyder | 424/442 |
| 3,907,883 | 9/1975 | Welton | 562/590 |
| 4,166,865 | 9/1979 | Sakamoto et al. | 514/450 |
| 4,192,875 | 3/1980 | Veber et al. | 514/11 |
| 4,336,250 | 6/1982 | Scheifinger | 514/9 |
| 4,430,328 | 2/1984 | Scheifinger | 514/8 |
| 4,431,801 | 2/1984 | Celmer et al. | 536/123 |

*Primary Examiner*—Thurman Page
*Assistant Examiner*—William E. Benston, Jr.
*Attorney, Agent, or Firm*—Thomas R. Savitsky; William P. Heath, Jr.

[57] ABSTRACT

Novel diamides having a nitrogen-containing heterocyclic moiety such as pyridyl are disclosed that are useful for improving feed utilization efficiency of ruminants and for improving lactation of lactating ruminants.

28 Claims, No Drawings

NOVEL DIAMIDES AND METHOD FOR IMPROVING FEED UTILIZATION AND LACTATION IN RUMINANT ANIMALS

This is a divisional of copending application Ser. No. 07/297,898 filed on Jan. 17, 1989 Now U.S. Pat. No. 4,895,951, which application is a continuation-in-part of application Ser. No. 81,048, filed Aug. 3, 1987 and now abandoned.

FIELD OF THE INVENTION

The invention relates to novel compounds and methods for improving feed utilization and lactation in ruminant animals. In particular, the invention relates to novel diamides having a nitrogen containing heterocyclic moiety and to methods of improving ruminant feed utilization and lactation by administering one or more of said diamides.

BACKGROUND OF THE INVENTION

It is well established that improvements in feed utilization efficiency in ruminant animals can be achieved by altering the fermentation process which takes place in the rumen. Ruminant animals utilize their food by degrading the carbohydrates contained therein to pyruvate and metabolizing the pyruvate to volatile fatty acids (VFAs) such as acetate, propionate and butyrate. These VFAs are absorbed from the gut and are employed for energy production which can then be channeled into growth, lactation, etc., by the ruminant.

The process of formation of acetate in the rumen is one of the major inefficiencies in the digestive process. Since acetate is made by the degradation of a pyruvate molecule, each molecule of acetate which is produced is accompanied by a one carbon molecule which subsequently results in the formation of methane. Most of the methane produced is lost through eructation. Since butyrate is made from two molecules of acetate, each molecule of butyrate involves the loss to the animal of two molecules of methane, with all of the associated energy.

Thus, the efficiency of carbohydrate utilization (carbohydrates being the major nutritive portion of ruminant animals' feed) can be increased by treatments which encourage the animal to produce propionate rather than acetate or butyrate from carbohydrates. Further, the efficiency of feed use can be effectively monitored by observing the production and concentration of propionate in the rumen. If the animal is making more propionate, it will be found to be using its feed more efficiently. A reduction in the amount of methane produced has also been observed to be a good indication of increased feed efficiency.

In this regard, compounds which increase the amount of propionate produced by a ruminant animal enhance the efficiency of feed utilization and have been observed to provide many beneficial results. For instance, it has been disclosed that administration of certain antibiotics which promote production of propionate can be used to promote growth rates of ruminant animals (see, e.g., Celmer et al., U.S. Pat. No. 4,431,801; Maehr, U.S. Pat. No. 4,218,560). Additionally, propionate-increasing substances have also been helpful in improving milk production in lactating ruminants (e.g., Scheifinger, U.S. Pat. Nos. 4,430,328 and 4,336,250). It is thus highly desirable to develop compounds which can increase the production of propionate in ruminant animals such as cattle, sheep or goats in order to improve feed utilization by animals which will promote the growth of the animals and also achieve improved lactation as well.

SUMMARY OF THE INVENTION

The present invention is directed to novel diamides of the formula:

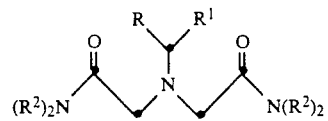

(I)

wherein R represents

(a)

wherein n is an integer of 0 to 2, and each X, independently, represents lower alkyl, lower alkoxy, chloro, acetyl, nitro, bromo or carboalkoxy;

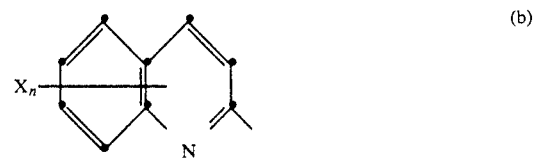

(b)

wherein n and each X, independently, have the same meaning as previously defined;

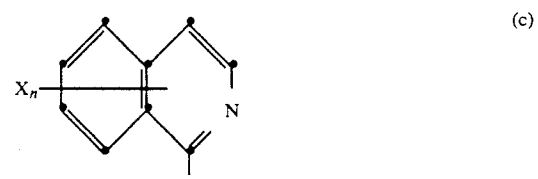

(c)

wherein n and each X, independently, have the same meaning as previously defined; or

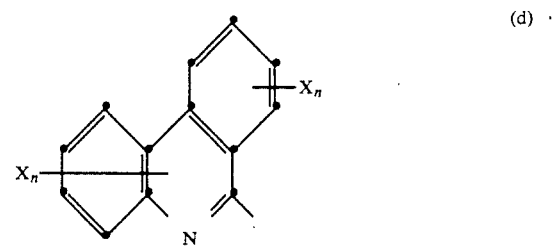

(d)

wherein each n, independently, and each X, independently, have the same meaning as previously defined; $R^1$ represents hydrogen, methyl or ethyl, and each $R^2$, independently, represents a straight or branched chain alkyl of 1 to 6 carbon atoms, or the physiologically acceptable salts thereof.

The present invention is also directed to a method for increasing the efficiency of feed utilization by ruminant animals comprising administering to said animals an effective amount of one or more compounds of Formula I.

Also included is a method for improving lactation in lactating ruminant animals comprising administering to said animals a lactation improving amount of one or more compounds of Formula I.

Compositions comprising one or more compounds of Formula I with an inert carrier are also within the scope of the invention.

Preferably, in the compound of Formula I, n will be 0 or 1, with 0 being most preferred; R will be 2-pyridyl; $R^1$ will be hydrogen; and $R^2$ will be an alkyl group of three to five carbon atoms such as tert-butyl, isobutyl, n-butyl or isopropyl. The most preferred compound is (2,2'[[(2-pyridyl)-methyl]-imino] bis[N,N-bis(2-methylpropyl)-acetamide]). As used herein, the term "effective amount" refers to that amount of one or more compounds of the invention, when administered to a ruminant animal, that is sufficient to increase the growth rate and/or feed conversion efficiency of the treated ruminant animals without resulting in any significant adverse side effect; the term "lactation improving amount" refers to that amount of one or more compounds of the invention, when administered to a lactating ruminant, that is sufficient to cause an observable improvement in milk production without resulting in any significant adverse side effects; the term "lower alkyl" refers to straight chain or branched alkyl moieties of 1 to 6 carbon atoms; the term "lower alkoxy" refers to alkoxy moieties of 1 to 6 carbon atoms, and the term "carboalkoxy" refers to carboalkoxy moieties of 2 to 7 carbon atoms.

DETAILED DESCRIPTION OF THE INVENTION

The diamides of the present invention can be prepared in two steps. The first step involves forming a chloroamide compound of the formula:

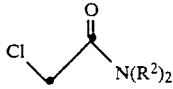   (II)

wherein $R^2$ has the same meaning as previously defined, by reacting chloroacetyl chloride with an appropriate amine compound of the formula:

   (III)

wherein $R^2$ has the same meaning as previously defined.

The reaction is carried out in a suitable solvent such as diethyl ether for a time and at a temperature sufficient to form the desired chloroamide compound of Formula II. A typical temperature is between about $-10°$ C. and room temperature and a typical time is about 1 hour.

The second step involves forming the desired compound of Formula I by reacting an appropriate chloroamide compound of Formula II with a compound of the formula:

   (IV)

wherein R and $R^1$ have the same meaning as previously defined. The reaction occurs, typically under an inert gas such as argon or nitrogen, in the presence of a suitable base such as diisopropylethylamine, diisobutylamine, triethylamine, or the like in a suitable solvent medium such as dimethoxyethane for a time and at a temperature sufficient to form the desired diamide of Formula I. A typical temperature is about reflux and a typical time is about 16-24 hours.

The compound of Formula IV can be prepared by procedures that are the same or similar to those known in the art. For example, compounds of Formula IV can be prepared by reduction of the corresponding nitriles or oximes as described by J. March in "Advanced Organic Chemistry," McGraw Hill Books Company, 2nd edition, pp. 834-835.

The salts of the compounds of this invention are physiologically acceptable salts derived from physiologically acceptable acids. Such physiologically acceptable acids include inorganic acids, e.g., hydrochloric acid, nitric acid, phosphoric acid, sulfuric acid, hydrobromic acid, hydroiodic acid, nitrous acid, phosphorous acid, and the like, as well as organic acids, such as aliphatic mono- or dicarboxylic acids, phenyl-substituted alkanecarboxylic acids, hydroyalkanecarboxylic acids or alkanedicarboxylic acids, aromatic acids, aliphatic or aromatic sulfonic acids, and the like.

Physiologically acceptable salts of these acids include therefore, for example, the sulfate, pryosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propionate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, beta-hydroxybutyrate, glycollate, malate, tartrate, methanesulfonate, propanesulfonate, naphthalene-1-sulfonate, naphthalene-2-sulfonate, and the like.

The salts of the diamide of the present invention can be prepared according to procedures commonly employed for the preparation of anionic salts. For example, the free base form of a diamide compound is dissolved in a suitable solvent, and an aqueous or organic solution of the desired acid is added to the diamide solution. The diamide anionic salts can be isolated by filtration and recrystallization or by evaporation of the solvent and purification.

In the present invention, an effective amount of diamide compound is administered to a ruminant animal in order to improve the efficiency of feed utilization by the animal. It is well established that the administration of substances which improve feed utilization efficiency through increases in propionate production also acts to improve growth rates in ruminant animals. The improved growth rates result from the additional energy made available by the more efficient processing of feed. Therefore the feed utilization method of the invention also emcompasses growth promotion activity.

It has been further established that propionate-increasing compounds which improve feed utilization efficiency can also be effective in increasing milk production in lactating ruminant animals. In the lactating ruminant, energy for lactation is often the most limiting factor in milk production, and improvements in feed utilization efficiency often provide the energy needed for increased lactation. However, improving feed utilization by increasing the animal's production of propionate will not always ensure that the milk produced by the lactating ruminant will be of sufficient quality. In milk production, acetate is required in order to synthesize milk fat, while propionate is utilized to produce glucose, and has very little effect on the milk fat produced. In addition, butyrate is degraded into acetate units and then it too can be used in long chain fatty acids synthesis producing the milk fat.

Accordingly, in order to increase milk production in lactating ruminants it is necessary to increase production of propionate, but not at the expense of significant decreases in acetate or butyrate production. Significant reductions in acetate and butyrate production result in a milk product of reduced milk fat content, rendering the milk less economically desirable in the United States (at the present time). It is necessary, therefore, that a compound desirable for use in promoting lactation be one that improves propionate production without significantly lowering acetate and butyrate levels.

The diamide compounds of the present invention provide a significant increase in propionate levels without causing a significant decrease in acetate or butyrate levels, and thus can be used to promote lactation in lactating ruminants. A method of improving lactation in ruminants is thereby provided which comprises administering to lactating ruminant animals a lactation improving amount of one more diamide compounds of the present invention. The administration of the diamide(s) may be direct, or a composition for promoting lactation may be prepared which comprises a lactation-promoting amount of diamide of Formula I and an inert carrier.

It is not desired to be bound by any particular mechanism or theory, however, the diamide compounds of the present invention are believed to function by selectively inhibiting the growth of a number of species of bacteria which are commonly found in the rumen of ruminant animals. When included in a growth medium designed to support the growth of pure rumen bacterial species, one or more diamides inhibit growth of microorganisms such as *Ruminococcus flavefaciens, Butyrivibrio fibrisolvens, Streptococcus bovis*, and the like. In contrast, organisms such as *Selenomonas ruminantium* usually are only slightly affected. In general, the diamide compounds of the present invention seem more active against gram positive bacteria than gram negative bacteria.

The diamide compounds of the present invention can be administered to increase feed utilization efficiency of ruminants in any way which ensures that the animals receive an effective amount of one or more of the desired compounds. It is preferred that one or more compounds be administered orally and at an effective amount of from about 0.2 to about 100 milligrams (mg) per kilogram (kg) of ruminant body weight per day. It is particularly preferred that the effective amount is between about 1 to about 10 mg/kg of body weight per day of one or more diamide compounds of the present invention.

The diamide compounds of the present invention can be administered to improve lactation of lactating ruminants in any way which ensures that the animals receive a lactation improving amount of one or more of the desired compounds. A lactation improving amount is typically that amount that results in an increase in the volume of milk produced by about 2 to about 15 percent relative to untreated animals. It is preferred that one or more compounds be administered orally and at a lactation improving amount of from about 0.2 to about 100 mg/kg of ruminant body weight per day. It is particularly preferred that the lactation improving amount is between about 1 and about 10 mg/kg of body weight per day of one or more diamide compounds of the invention.

The exact effective amount and/or lactation improving amount of one or more diamides to be employed will vary depending upon factors such as species of animal, or the size, weight, age and health of the animal. In particular cases, the concentration can be determined by conventional dose titration techniques.

The most practical way to administer the diamide compound of the present invention is to add an effective amount (or lactation improving amount) of one or more diamides into the animal's feed. This can be done by directly adding a desired amount of the diamide(s) to the feed supply, or by first forming the compound(s) into a premix composition for subsequent addition to the feed. Such a composition preferably comprises one or more diamide compounds of Formula I above, along with an inert carrier, the amount of diamide(s) being sufficient to result in increased feed utilization and/or improved lactation in an appropriate ruminant animal upon administration to said animal. Suitable carriers include ground corn, barley, soybean meal, wheat, soy flour, or any similar low-priced, edible material. It is desired that the amount of one or more diamide compounds used in the composition be sufficient to comprise from about 5 to about 1000 parts per million in the animal feed. It is particularly preferred that the diamide comprises from about 30 to about 300 parts per million of the ultimate animal feed.

The form of the additive to the feed is not crucial, and alternative forms for administering the diamide compound may be employed. For instance, the compound can be incorporated into tablets, drenches, salt blocks, paste, boluses, or capsules and doped to the animals. Formulation of the compounds in such dosage forms can be accomplished by means of methods well known in the veterinary pharmaceutical art. Each individual dosage unit should contain a quantity of the compound which has a direct relation to the proper daily dose for the animal to be treated, as discussed above.

The following examples are provided in order to further illustrate the present invention and should not be construed as limiting the invention in any way.

EXAMPLE 1

Preparation of Chloroacetic Acid, N,N-diisobutylamide

To a suspension of diisobutylamine (110 g, 149 mL), sodium carbonate (80 g) and ether (400 mL) at $-10°$ C. was added chloroacetyl chloride (85 g, 0.75 mol). The reaction mixture was maintained below room temperature during the addition. The mixture was stirred for 45 minutes after the addition was complete. The solid was removed by filtration, and the filtrate was concentrated resulting in a residue. The residue was dissolved in methylene chloride, extracted with 1N HCl followed by dilute sodium carbonate and dried over solid sodium sulfate which resulted in an aqueous and organic layer. Concentration of the organic layer afforded 80.8 g of a light yellow liquid. The NMR spectrum of this light yellow liquid was consistent with the desired product and indicated that the compound was >95% pure.

EXAMPLE 2

Preparation of 2-Chloro-N,N-dihexylacetamide

This chloroamide was prepared by the general procedure described in Example 1 using chloroacetyl chloride (0.11 mol), dihexylamine (0.13 mol), diisopropylethlamine (0.13 mol) and ether (200 mL). The residue was purified by distillation (100° C., 0.05 mm) to provide 19 g of a light yellow oil.

EXAMPLE 3

Preparation of 2-Chloro-N,N-diethylacetamide

This chloroamide was prepared by the general procedure described in Example 1 using chloroacetyl chloride (0.20 mol), diethylamine (0.22 mol), diisopropylethylamine (0.22 mol) and ether (200 mL). The residue was purified by distillation (60°-70° C., 2 mm) to provide 18 g of light yellow oil.

EXAMPLE 4

Preparation of 2-Chloro-N-1,1,3,3-tetramethylbutyl)acetamide

This chloroamide was prepared by the general procedure described in Example 1 using chloroacetyl chloride (0.15 mol), 1,1,3,3-tetramethylbutylamine (0.18 mol), diisopropylethylamine (0.18 mol) and ether (200 mL). The residue was purified by distillation (50° C., 0.05 mm) to provide 16 g of product.

EXAMPLE 5

Preparation of 2-Chloro-N,N-dioctylacetamide

This chloroamide was prepared by the general procedure described in Example 1 using chloroacetyl chloride (0.40 mol), dioctylamine (0.40 mol), sodium carbonate (0.41 mol) and ether (400 mL). The light yellow oil was used without further purification.

EXAMPLE 6

Preparation of 2-Chloro-N,N-diisopropylacetamide

This chloroamide was prepared by the general procedure described in Example 1 using chloroacetyl chloride (0.28 mol), diisopropylamine (0.32 mol), sodium carbonate (0.28 mol) and ether (200 mL). The residue was purified by distillation (100° C., 0.20 mm) to provide 17 g of pure product.

EXAMPLE 7

Preparation of 2-Chloro-N,N-dibutylacetamide

This chloroamide was prepared by the general procedure described in Example 1 using chloroacetyl chloride (0.24 mol), dibutylamine (0.27 mol) and ether (200 mL). No additional base was used in this reaction. The yellow oil was used without further purification.

EXAMPLE 8

Preparation of (2,2'[[(2-pyridyl)methyl]-imino]bis [N,N-bis(2-methylpropyl)acetamide])

A solution of 2-(aminomethyl)pyridine (1.10 g, 0.0101 mol), 2-chloro-N,N-diisobutylacetamide (6.25 g, 0.030 mol), diisopropylethylamine (DIEA, 6.5 g, 0.030 mol), and dimethoxyethane (DME, 20 mL) was heated to reflux under argon for 16 hours. The solution was allowed to cool, and the solvent was removed. The remaining material was partitioned between methylene chloride and 10% HCl. The aqueous layer was made basic and extracted with ethyl acetate. This organic layer was concentrated to give 3.67 g of residue. Substantial amounts of product are often isolated from the initial methylene chloride layer. The residue was purified by Kugelrohr distillation. The product, a light yellow oil (3.54 g), distilled at 150° C. @ 0.5 mm of Hg. The NMR spectrum, infrared spectrum, and the field desorption mass spectrum (FDMS) of the distilled material are consistent with the desired product.

EXAMPLE 9

Preparation of 2-(Aminomethyl)pyridinediacetic acid, bis(N,N-diethylamide)

Pyridine diamide 2 was prepared according to the general procedure described in Example 8 using 2-(aminomethyl)pyridine (0.015 mol), 2-chloro-N,N-diethylacetamide (0.045 mol), diisopropylethylamine (0.060 mol) and dimethoxyethane (25 mL). The product was isolated from the methylene chloride extraction of the basic aqueous layer. The residue was distilled (140° C., 0.10 mm) to afford 3.7 g of pure product.

EXAMPLE 10

Preparation of 2-(Aminomethyl)pyridinediacetic acid, bis(N,N-dihexylamide)

Pyridine diamide 3 was prepared according to the general procedure described in Example 8 using 2-(aminomethyl)pyridine (0.015 mol), 2-chloro-N,N-dihexylacetamide (0.048 mol), diisopropylethylamine (0.033 mol) and dimethoxyethane (25 mL). The product was isolated from a heptane extraction of the acidic aqueous layer. The product was made basic by extraction with aqueous NaOH. The organic solution was concentrated, and the residue was distilled (200° C., 0.05 mm) to afford 6.1 g of pure product.

EXAMPLE 11

Preparation of 2-(Aminomethyl)pyridinediacetic acid, bis(N-(1,1,3,3-tetramethylbutyl)amide)

Pyridine diamide 4 was prepared according to the general procedure described in Example 8 using 2-(aminomethyl)pyridine (0.011 mol), 2-chloro-N-(1,1,3,3-tetramethylbutyl)acetamide (0.033 mol), diisopropylethylamine (0.025 mol) and dimethoxyethane (25 mL). The product was isolated from the methylene chloride extraction of the acidic aqueous layer. The product was made basic by extraction of the methylene chloride solution with aqueous NaOH. The methylene chloride solution was concentrated, and the residue was distilled (150° C., 0.03 mm) to afford 3.7 g of pure product.

EXAMPLE 12

Preparation of 2-(Aminomethyl)pyridinediacetic acid, bis(N,N-dioctylamide)

Pyridine diamide 5 was prepared according to the general procedure described in Example 8 using 2-(aminomethyl)pyridine (0.019 mol), 2-chloro-N,N-dioctylacetamide (0.056 mol), diisopropylethylamine (0.056 mol) and dimethoxyethane (30 mL). The product was isolated from the heptane extraction of the acidic aqueous layer. The product was made basic by extraction with aqueous NaOH. The organic solution was concentrated, and the residue was distilled (150°-200° C., 0.10 mm).

EXAMPLE 13

Preparation of 2-(Aminomethyl)pyridinediacetic acid, bis(N,N-dibutylamide)

Pyridine diamide 6 was prepared according to the general procedure described in Example 8 using 2-(aminomethyl)pryidine (0.010 mol), 2-chloro-N,N-dibutylacetamide (0.030 mol), diisopropylethylamine (0.030 mol) and dimethoxyethane (30 mL). The product was isolated from the methylene chloride extraction of the acidic aqueous layer. The product was made basic by extraction with aqueous NaOH. The organic solution was concentrated, and the residue was distilled (150°–200° C., 0.10 mm) to afford 3.6 g of product.

EXAMPLE 14

Preparation of 2-(Aminomethyl)pyridinediacetic acid, bis(N,N-diisopropylamide)

Pyridine diamide 7 was prepared according to the general procedure described in Example 8 using 2-(aminomethyl)pyridine (0.013 mol), 2-chloro-N,N-diisopropylacetamide (0.038 mol), diisopropylethylamine (0.038 mol) and dimethoxyethane (25 mL). The product was isolated from both the methylene chloride extraction of the acidic aqueous layer and the heptane extraction of the basic layer in about equal amounts. Mass spectral analysis of the two layers showed the material in the heptane layer to be of greater purity. The residue from the heptane layer was distilled (150° C., 0.05 mm) to afford 2.2 g of product.

EXAMPLE 15

Effect of Diamide Compound on Rumen Bacterial Growth

The compound of Example 8 above was placed in a growth culture medium of five rumen bacterial species, and growth of the treated cultures was monitored and compared with growth in control media. The results are presented in Table 1 below. The diamide compound of the present invention substantially prevented the growth of *R. flavefaciens, B. fibrisolvens, R. albus, S. bovis, B. ruminocola, L. vitulinus, E. limosum,* and *B. succinogenes,* and *E. ruminantium.* In addition, the growth of *M. elsdenii* and *B. amylophilus* was slightly inhibited. The growth of *S. ruminantium* was almost unaffected by the diamide. In general, the diamide appeared to be more active against gram-positive bacteria than gram-negative bacteria.

TABLE 1

| BACTERIA | | $OD_{660}$[1] | $SD$[2] | RESPONSE[3] |
|---|---|---|---|---|
| *Ruminococcus flavefaciens* | control | 0.86 | 0.03 | 0.0 |
| | w/diamide | 0.01 | 0.01 | 98.6 |
| *Butyrivibrio fibrisolvens* | control | 1.27 | 0.04 | 0.0 |
| | w/diamide | −0.09 | 0.01 | 106.9 |
| *Ruminococcus albus* | control | 1.27 | 0.00 | 0.0 |
| | w/diamide | −0.03 | 0.01 | 122.1 |
| *Lactobacillus vitulinus* | control | 1.72 | 0.03 | 0.0 |
| | w/diamide | 0.02 | 0.01 | 99.0 |
| *Eubacterium ruminantium* | control | 1.47 | 0.17 | 0.0 |
| | w/diamide | 0.23 | 0.39 | 84.6 |
| *Eubacterium limosum* | control | 1.26 | 0.02 | 0.0 |
| | w/diamide | 0.04 | 0.04 | 96.6 |
| *Megasphera elsdenii* | control | 0.67 | 0.05 | 0.0 |
| | w/diamide | 0.58 | 0.04 | 13.0 |
| *Bacteroides amylophilus* | control | 0.50 | 0.01 | 0.0 |
| | w/diamide | 0.40 | 0.22 | 19.5 |
| *Bacteroides succinogenes* | control | 0.89 | 0.03 | 0.0 |
| | w/diamide | −0.05 | 0.01 | 105.7 |
| *Streptococcus bovis* | control | 1.80 | 0.03 | 0.0 |
| | w/diamide | 0.08 | 0.09 | 95.6 |
| *Bacteroides ruminicola* | control | 1.55 | 0.04 | 0.0 |
| | w/diamide | −0.20 | 0.01 | 112.9 |
| *Selenomonas ruminantium* | control | 1.74 | 0.01 | 0.0 |
| | w/diamide | 1.69 | 0.06 | 2.8 |

[1]Each value is the mean of triplicate samples.
[2]SD is the standard deviation.
[3]Responses represent inhibition of growth as a percent of the controls and are calculated as follows: Response = 100 × (1-(experimental optical density at 660 nanometers ($OD_{660}$)/control $OD_{660}$))

EXAMPLE 16

Fermentation Experiments

Rumen bacterial suspensions were prepared using rumen fluid obtained from a cannulated steer. The rumen fluid was mixed in a Waring blender under $CO_2$ for one minute and then strained through four layers of cheesecloth. The strained fluid was then diluted with three volumes of a suitable growth medium to obtain final bacterial suspensions. Various levels of the diamide (of Example 8) from 1 mg/mL solutions or suspensions in methanol were added to 50-mL vials. The methanol was evaporated by drying in a 39° C. oven for 24 hours, and 0.4 g of chopped, dried alfalfa (sieved, 1 mm mesh) was added to each vial. The final bacterial suspensions obtained as described above were added to the vials, 20 mL of suspension per vial, and the suspensions were incubated for 20 hours with an aerobic $CO_2$ atmosphere, shaking at 39° C.

The suspensions were then processed for determination of volatile fatty acids (VFA). The VFAs were determined by the following procedure. After filtration of the VFA sample through 0.2 micron filters to remove particulate matter, samples were transferred to 2-mL vials. The VFA concentrations of the samples were determined by GLC, using a Hewlett Packard (HP) 5880 gas chromatograph on a 2-meter glass column packed with 0.3% Carbowax 20M on Carbopack C. Injector and detector temperatures were set at 200° C. while the oven temperature was programmed from 85° to 140° C. at 4° C. per minute. Carrier flow rate was set at 25 mL per minute. The results of the VFA determinations are presented in Table 2.

The results indicated that the diamide compound was responsible for an increase in the level of propionate in the rumen bacterial suspension, and this increase was greater with a larger dosage of the diamide. In addition, there was no decrease in acetate level and there was a decrease in butyrate level.

TABLE 2

VFA CONCENTRATIONS IN TREATED BACTERIAL SUSPENSIONS
Concentrations of VFAs (millimoles per liter)
SD = Standard Deviation

| Micrograms of Diamide per mL | Acetic | SD | Propionic | SD | Butyric | SD | Total VFA | SD |
|---|---|---|---|---|---|---|---|---|
| 0 | 71.7 | 5.5 | 46.6 | 3.1 | 20.3 | 1.3 | 138.6 | 8.5 |
| 2.5 | 68.0 | 4.8 | 45.1 | 4.3 | 18.4 | 1.1 | 131.5 | 9.0 |
| 5 | 75.7 | 4.7 | 49.0 | 3.0 | 20.1 | 1.6 | 144.8 | 7.5 |
| 10 | 68.1 | 4.7 | 48.8 | 4.2 | 17.4 | 1.2 | 134.3 | 8.8 |
| 20 | 78.6 | 7.8 | 68.3 | 6.9 | 14.4 | 1.8 | 161.3 | 14.4 |
| 40 | 80.7 | 17.0 | 81.8 | 14.0 | 7.0 | 1.8 | 169.5 | 31.0 |

I claim:

1. A method for improving lactation in lactating ruminant animals comprising administering to said animals a lactation improving amount of a compound of the formula:

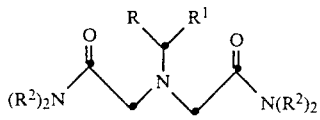

wherein R represents

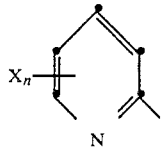

(a)

wherein n is an integer of 0 to 2, and each X, independently, represents lower alkyl, lower alkoxy, chloro, acetyl, nitro, bromo or carboalkoxy;

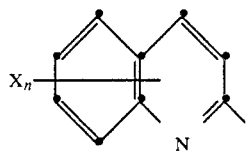

(b)

wherein n and each X, independently, have the same meaning as previously defined;

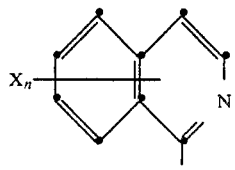

(c)

wherein n and each X, independently, have the same meaning as previously defined; or

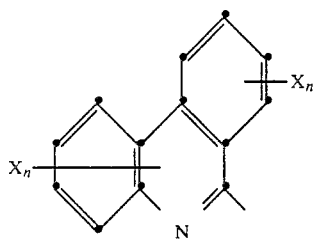

(d)

wherein each n, independently, and each X, independently, have the same meaning as previously defined; $R^1$ represents hydrogen, methyl or ethyl, and each $R^2$, independently, represents a straight or branched chain alkyl of 1 to 6 carbon atoms, or the physiologically acceptable salts thereof.

2. The method of claim 1 wherein R is 2-pyridyl.

3. The method of claim 1 wherein R is 2-pyridyl and $R^1$ is hydrogen.

4. The method of claim 1 wherein R is 2-pyridyl, $R^1$ is hydrogen and each $R^2$ is, independently, an alkyl group of 3 to 5 carbon atoms.

5. The method of claim 1 wherein R is 2-pyridyl, $R^1$ is hydrogen and each $R^2$ is, independently, tert-butyl, isobutyl, n-butyl or isopropyl.

6. The method of claim 1 wherein R is 2-pyridyl, $R^1$ is hydrogen and $R^2$ is isobutyl.

7. The method of claim 1 wherein R is 2-quinolinyl, $R^1$ is hydrogen and $R^2$ is isobutyl.

8. A composition for promoting the growth of ruminant animals comprising an effective amount of a compound of the formula:

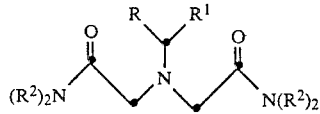

wherein R represents

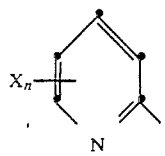

(a)

wherein n is an integer of 0 to 2, and each X, independently, represents lower alkyl, lower alkoxy, chloro, acetyl, nitro, bromo or carboalkoxy;

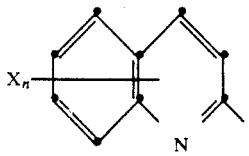
(b)

wherein n and each X, independently, have the same meaning as previously defined;

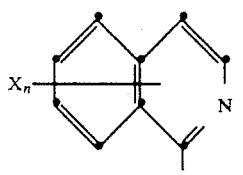
(c)

wherein n and each X, independently, have the same meaning as previously defined; or

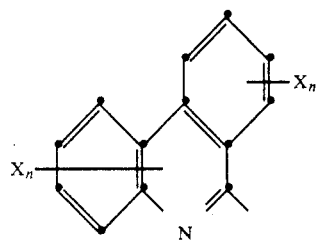
(d)

wherein each n, independently, and each X, independently, have the same meaning as previously defined; $R^1$ represents hydrogen, methyl or ethyl, and each $R^2$, independently, represents a straight or branched chain alkyl of 1 to 6 carbon atoms, or the physiologically acceptable salts thereof and, an inert edible carrier; and wherein said effective amount is sufficient to comprise from about 5 to about 1000 parts per million in said composition.

9. The composition of claim 8 wherein R is 2-pyridyl.

10. The composition of claim 8 wherein R is 2-pyridyl and $R^1$ is hydrogen.

11. The composition of claim 8 wherein R is 2-pyridyl, $R^1$ is hydrogen and each $R^2$ is, independently, an alkyl group of 3 to 5 carbon atoms.

12. The composition of claim 8 wherein R is 2-pyridyl, $R^1$ is hydrogen and each $R^2$ is, independently, tert-butyl, isobutyl, n-butyl or isopropyl.

13. The composition of claim 8 wherein R is 2-pyridyl, $R^1$ is hydrogen and $R^2$ is isobutyl.

14. The composition of claim 8 wherein R is 2-quinolinyl, $R^1$ is hydrogen and $R^2$ is isobutyl.

15. The method of claim 1 wherein said compound is administered orally.

16. The composition of claim 8 wherein said effective amount is between about 30 and 300 parts per million of the ultimate formulation.

17. A method for increasing the efficiency of feed utilization by ruminant animals comprising administering to said animals an effective amount of a compound of the formula:

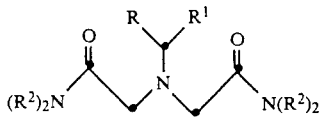

wherein R represents

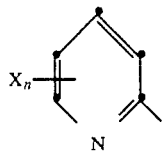
(a)

wherein n is an integer of 0 to 2, and each X, independently, represents lower alkyl, lower alkoxy, chloro, acetyl, nitro, bromo or carboalkoxy;

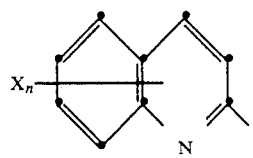
(b)

wherein n and each X, independently, have the same meaning as previously defined;

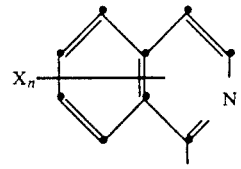
(c)

wherein n and each X, independently, have the same meaning as previously defined; or

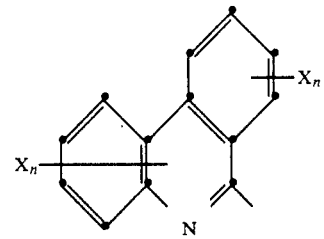
(d)

wherein each n, independently, and each X, independently, have the same meaning as previously defined; $R^1$ represents hydrogen, methyl or ethyl, and each $R^2$, independently, represents a straight or branched chain alkyl of 1 to 6 carbon atoms, or the physiologically acceptable salts thereof.

18. The method of claim 17 wherein R is 2-pyridyl.

19. The method of claim 17 wherein R is 2-pyridyl and $R^1$ is hydrogen.

20. The method of claim 17 wherein R is 2-pyridyl, $R^1$ is hydrogen and each $R^2$ is, independently, an alkyl group of 3 to 5 carbon atoms.

21. The method of claim 17 wherein R is 2-pyridyl, $R^1$ is hydrogen and each $R^2$ is, independently, tert-butyl, isobutyl, n-butyl or isopropyl.

22. The method of claim 17 wherein R is 2-pyridyl, $R^1$ is hydrogen and $R^2$ is iso-butyl.

23. The method of claim 17 wherein R is 2-quinolinyl, $R^1$ is hydrogen and $R^2$ is iso-butyl.

24. The method of claim 17 wherein said compound is administered orally.

25. The method of claim 17 wherein said effective amount is between about 0.2 and 100 mg per kg of body weight per day.

26. The method of claim 17 wherein said effective amount is between about 1 and 10 mg per kg of body weight per day.

27. The method of claim 1 wherein said lactation improving amount is between about 0.2 and 100 mg per kg of body weight per day.

28. The method of claim 1 wherein said lactation improving amount is between about 1 and 10 mg per kg of body weight per day.

* * * * *

UNITED STATES PATENT AND TRADEMARK OFFICE
CERTIFICATE OF CORRECTION

PATENT NO. : 5,041,452
DATED : August 20, 1991
INVENTOR(S) : Alan W. White

It is certified that error appears in the above-identified patent and that said Letters Patent is hereby corrected as shown below:

Column 12, lines 15-27, the structure should read:

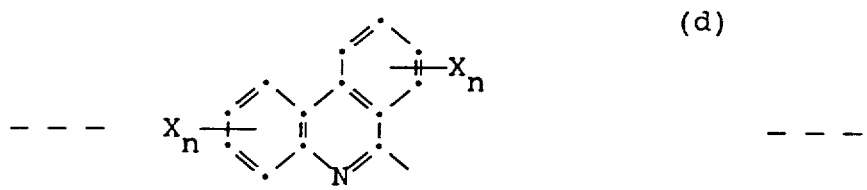

Column 13, lines 24-33, the structure should read:

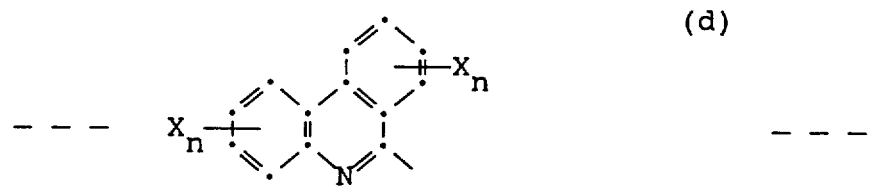

UNITED STATES PATENT AND TRADEMARK OFFICE
CERTIFICATE OF CORRECTION

PATENT NO. : 5,041,452
DATED : August 20, 1991
INVENTOR(S) : Alan W. White

It is certified that error appears in the above-identified patent and that said Letters Patent is hereby corrected as shown below:

Column 14, lines 43-52, the structure should read:

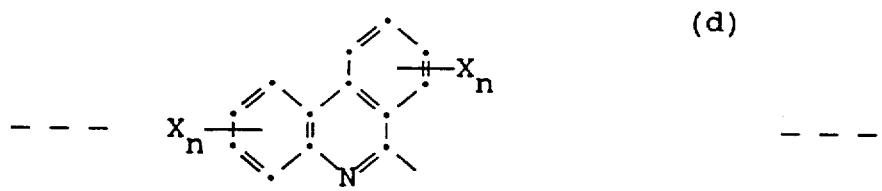

(d)

Signed and Sealed this

Twenty-third Day of March, 1993

Attest:

STEPHEN G. KUNIN

Attesting Officer     Acting Commissioner of Patents and Trademarks